(12) United States Patent
Behringer et al.

(10) Patent No.: US 9,580,455 B2
(45) Date of Patent: Feb. 28, 2017

(54) PROCESS FOR THE RECOVERY OF BETA ACETYLFURANOSIDE

(71) Applicant: Hoffmann-La Roche Inc., Nutley, NJ (US)

(72) Inventors: Martin Behringer, Bobenheim-Roxheim (DE); Bernd Junghans, Edingen-Neckarhausen (DE); Bernhard Knipp, Kuerten-Olpe (DE); Bernhard Pfeil, Ludwigshafen (DE); Gerald Zieres, Worms (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 194 days.

(21) Appl. No.: 13/675,220

(22) Filed: Nov. 13, 2012

(65) Prior Publication Data

US 2013/0072674 A1 Mar. 21, 2013
US 2016/0333040 A9 Nov. 17, 2016

Related U.S. Application Data

(63) Continuation of application No. 12/690,167, filed on Jan. 20, 2010, now abandoned.

(30) Foreign Application Priority Data

Jan. 27, 2009 (EP) ..................................... 09151384

(51) Int. Cl.
*C07H 1/00* (2006.01)
*C07H 13/04* (2006.01)

(52) U.S. Cl.
CPC ............... *C07H 1/00* (2013.01); *C07H 13/04* (2013.01)

(58) Field of Classification Search
CPC .................................. C07H 1/00; C07H 13/04
See application file for complete search history.

(56) References Cited

U.S. PATENT DOCUMENTS

2008/0161583 A1 * 7/2008 Nicholas et al. ............. 549/333
2010/0190976 A1 * 7/2010 Behringer et al. ............ 536/127

FOREIGN PATENT DOCUMENTS

WO WO 2008105593 A1 * 9/2008 ............... C07H 1/00

OTHER PUBLICATIONS

Pierce et al., J. Am. Chem. Soc., 1985, 107, p. 2448-2456.*
Sattler et al., Thermal Separation Processes: Principles and Design, 2007, Wiley-VCH Verlag GmbH, Chapter 7 "Solvent Evaporation, Crystallization", p. 475-532.*
Kiss et al., Helvetica Chimica Acta 65 ( 1982).

* cited by examiner

*Primary Examiner* — Jonathan S Lau
(74) *Attorney, Agent, or Firm* — Tony Wei Peng

(57) ABSTRACT

There is provided an improved method for the recovery of residual, unseparated β-acetylfuranoside from reaction mixtures remaining from an initial synthesis of acetylfuranoside, which is in particular usable on a large industrial scale, more particularly in the production of capecitabine.

2 Claims, 1 Drawing Sheet

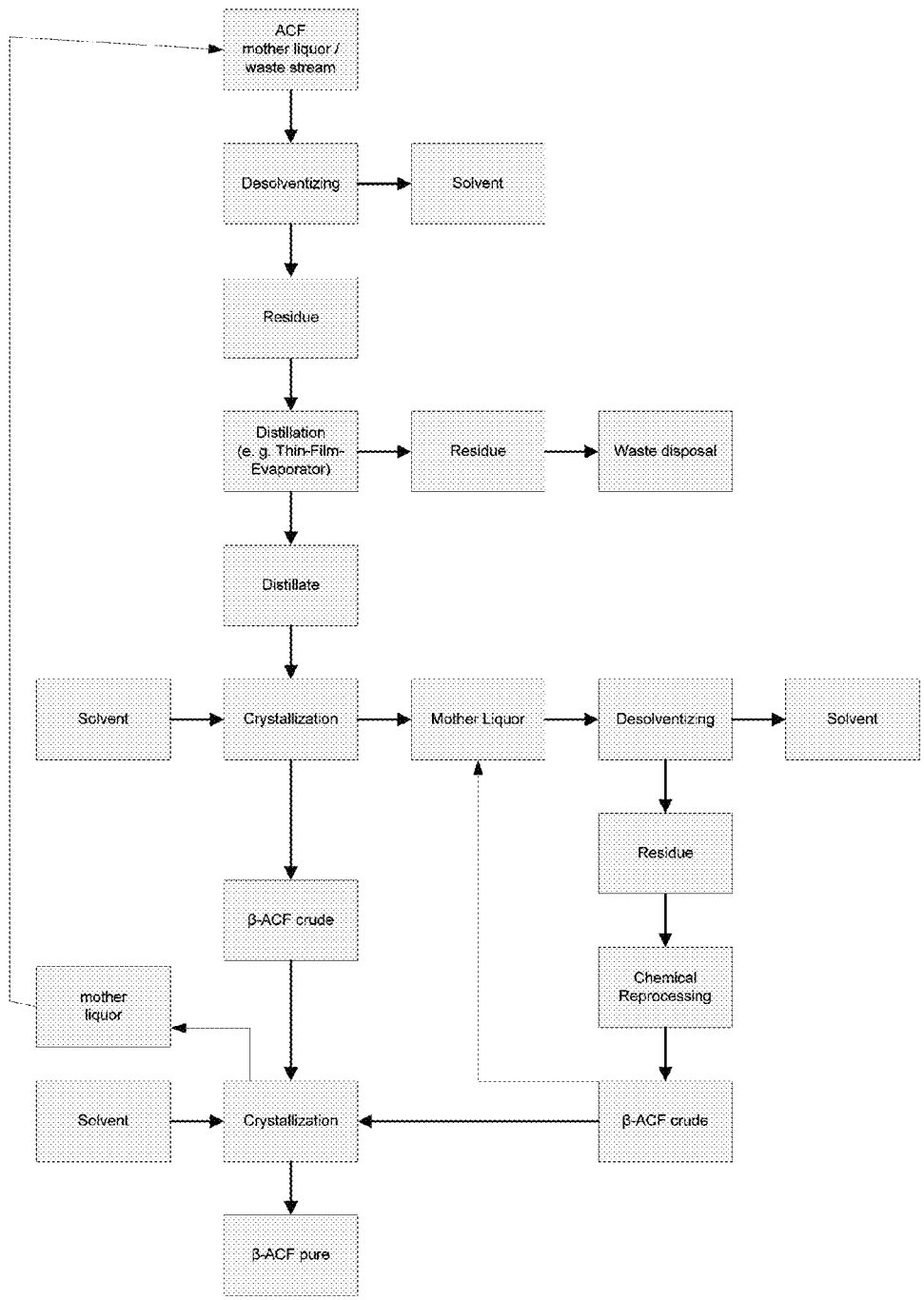
Process flow chart summarizing the process according to the present invention

PROCESS FOR THE RECOVERY OF BETA ACETYLFURANOSIDE

PRIORITY TO RELATED APPLICATION(S)

This application is a continuation of U.S. application Ser. No. 12/690,167, filed Jan. 20, 2010, now Pending, which claims the benefit of European Patent Application No. 09151384.6, filed Jan. 27, 2009, which is hereby incorporated by reference in its entirety.

The present invention is directed to a novel process for the recovery of further β-Acetylfuranoside (β-ACF, β-5-deoxy-1,2,3-tri-O-acetyl-D-ribofuranose) from mother liquors and process waste streams remaining from an initial synthesis of ACF.

BACKGROUND OF THE INVENTION

ACF can be prepared according to well known methods, as for example described in *Helvetica Chimica Acta*, Vol. 65(Nr. 149), *Fasc.* 5, 1982, 1531. The synthesis of ACF leads to a racemic mixture of α- and β-ACF which can be separated by selective crystallization and thus precipitation from the reaction mixture. Usually the β-ACF is the desired product, as it is a valuable starting material used in the manufacture of inter alia cytidine derivatives, such as capecitabine. Capecitabine is the active ingredient of the medicament Xeloda™. The ACF synthesis can be summarized according to the following reaction scheme 1:

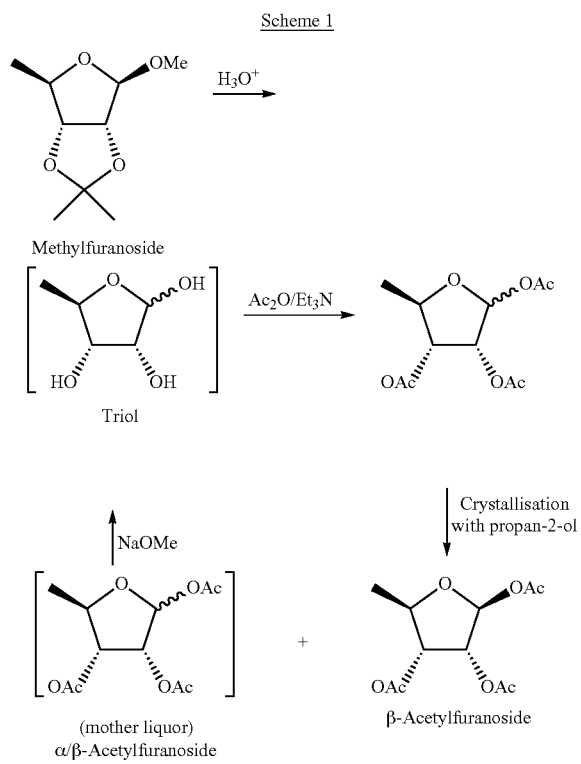

EP 0 021 231 as well as WO 2005/040184 disclose the further reaction of the unseparated ACF racemic mixture, containing both α- and β-ACF, to a final product. The separation is thus only carried out subsequent to the reaction of the β-anomer to the desired end product.

In any of the known methods the remaining, residual reaction mixture (mother liquor) contains about 8-15 weight-% of not precipitated α/β-Acetylfuranoside (ratio α:β is about 35:65), which is not separated from the reaction mixture. Consequently, and in particular when used on an industrial scale, considerable amounts of valuable β-ACF are wasted, huge amounts of waste residue have to be worked-up and the costs for the entire manufacturing process up to the final product rise significantly.

It is therefore the objective of the present invention to provide an improved method for the recovery of residual, unseparated β-ACF from reaction mixtures remaining from an initial synthesis of ACF, which is in particular usable on a large industrial scale, more particularly in the production of 5'-deoxy-5-fluoro-N-(pentyloxycarbonyl) cytidine (capecitabine). The advantages of the method according to the present invention are the increase of the overall yield of β-ACF, and consequently also of capecitabine per production cycle, thereby reducing the overall production costs. In addition, the present method renders the entire manufacturing more environmentally friendly due to avoiding of unnecessary high amounts of chemical waste. The method according to the present invention can also optionally be repeated in several serially connected cycles, thereby further improving the efficacy of the present method.

SUMMARY OF THE INVENTION

In one embodiment, the present invention provides a method for recovery of initially not separated β-ACF from mother liquor remaining from the synthesis of ACF, wherein the β-ACF is recovered by a combination of at least one distillation method and at least one chemical reaction step.

In a preferred embodiment the method according to the present invention comprises the following sequential reaction steps:

a) Evaporation to less than 1% residual solvent of the mother liquor remaining from an initial synthesis of ACF, to increase the content of residual α/β-ACF from about 8 to 15 weight-% to about 25 to 45 weight-%, followed by distillation to about 60 to 80 weight-% and subsequent crystallization of β-ACF out of the distillate by adding a suitable solvent;

b) Chemical conversion of α/β-ACF mixture remaining in the mother liquor of step a), to β-ACF by de-acetylation and subsequent re-acetylation, followed by crystallization of β-ACF by addition of a suitable solvent;

c) Optional repetition of step a) and b) in a sequential (clockwise) cyclic process.

In still another preferred embodiment according to the present invention, the distillation to about 60 to 80 weight-% in process step a) as described above is carried out at 1 to 3 mbar and 200 to 210° C. heating temperature in a continuous thin-film evaporator. The mixture which has to be distilled does surprisingly not decompose under these conditions though normally β-Acetylfuranoside begins to decompose at 150° C.

In yet another preferred embodiment there is provided the method as described above, wherein step b) comprises the de-acetylation of α/β-ACF in the presence of a suitable base, followed by neutralization with a suitable acid and further followed by the re-acetylation reaction in the presence of suitable base, a suitable catalyst and a suitable acetylating agent.

In a particularly preferred embodiment according to the present invention, the process step a) as described above is carried out according to the specific conditions as described in the accompanying Example 1; and the process step b) is carried out according to the specific conditions as described in the accompanying Example 2.

In another particularly preferred embodiment there is provided the process for recovery of β-ACF according to the present invention used during the manufacture of capecitabine.

DETAILED DESCRIPTION OF THE INVENTION

Definitions

The term "mother liquor" means any remaining mixture of residual starting materials or by-products left over after a main reaction product is isolated from that mixture in any step according to the present method. In particular, as used herein the term mother liquor means the remaining mixture subsequent to the synthesis of ACF according to scheme 1 above, which contains residual amounts of α/β-ACF together with a variety of impurities and by-products.

The term "distillation" or "distillation method" as used herein preferably means falling-film evaporator, molecular distillation, centrifugal molecular distillation, continuous simple distillation or related apparatus. A particularly preferred distillation method according to the present invention is the use of a thin-film evaporator.

The term "suitable solvent" in connection with the crystallization of β-ACF preferably means aliphatic alcohols, most preferably propan-2-ol.

The term "chemical reaction step" or "chemical conversion" as used herein means the conversion of the mixture of α- and β-Acetylfuranoside (α/β-ACF), which are both present in a ratio α:β of about 1:1, towards an increased amount of β-Acetylfuranoside by a series of chemical reaction steps, in particular by de-acetylation and subsequent re-acetylation.

The term "suitable base" in connection with the de-acetylation in step b) as described herein means alkali hydroxides or alkali alcoholates, preferably sodium methanolate (sodium methoxide).

The term "suitable acid" in connection with step b) as described herein means any conventional acid, preferably hydrochloric acid.

The term "suitable base" in connection with the re-acetylation in step b) as described herein means a base, preferably aliphatic or aromatic amines, most preferably triethylamine, n-methylpiperidine or pyridine.

The term "suitable acetylation agent" in connection with re-acetylation in step b) as described herein means acetic anhydride or acetyl halides, e. g. acetyl chloride.

The term "suitable catalyst" in connection with the re-acetylation in step b) as described herein means substituted amino-pyridines, preferably 4-dimethylaminopyridine.

The de-acetylation mentioned under step b) above is preferably carried out in aliphatic alcohols, in particular methanol, as solvents and at temperatures between 0 and −20° C., preferably −5 and −10° C. Subsequently, the reaction mixture is neutralized with a mineral acid, preferably hydrochloric acid, up to pH 4-6, preferably 5. The initial solvent, thus the aliphatic alcohol, is removed by distillation and replaced by a new solvent selected from chlorinated hydrocarbons, preferably methylenchloride or aromatic hydrocarbons, preferably toluene. Subsequently re-acetylation is carried out by the addition of a suitable amine, preferably triethylamine, 4-dimethylaminopyridine and acetic anhydride at temperatures of below 30° C., preferably 15° C. to 20° C.

Further details of the conditions for both steps a) and b) as described herein, together with appropriate work-up procedures, are given below and in particular by the accompanying working examples. The sequential use of steps a) and b), optionally followed by c), according to the specific parameters, temperature ranges, substances, solvents and conditions used in the disclosed working examples 1 and 2, respectively form a further particularly preferred embodiment according to the present invention.

The optional repetition of the sequential recovery cycle according to the present invention as mentioned under step c) above, can be carried out as many times as necessary. Possible limitations in the number of recovery cycles may arise from technical and chemical considerations, for example if no further β-ACF can be recovered or if the amount of recovered β-ACF becomes to small to justify the costs of the further continuation of the recovery cycle.

The essential process steps according to the present invention can be generally carried out as follows:

Distillative Recovery of β-Acetylfuranoside

Mother liquors and waste streams remaining from the chemical standard procedure to obtain β-ACF according to scheme 1 above, contain considerable amounts of α/β-Acetylfuranoside besides a variety of impurities and by-products.

After the mother liquor/waste stream solvent is removed ("Desolventizing") under reduced pressure (0 to 1000 mbar, preferably 0 to 200 mbar) and at 10 to 100° C., preferably 30 to 80° C., the obtained evaporation residue is feeded to a continuous or semi-continuous distillation as thin-film evaporator, falling-film evaporator, molecular distillation, centrifugal molecular distillation, continuous simple distillation or related apparatus. The use of a thin-film evaporator or molecular distillation is especially preferred.

The residue is than distilled under reduced pressure at 0 to 10 mbar, preferably 0 to 5 mbar, and 100-210° C. heating temperature (preferably 180-210° C.). The distillate can be used and processed as crude oil or is dissolved and crystallized from organic solvent (preferably propan-2-ol).

Chemical Conversion of ACF Mother Liquor

The conversion of α/β-Acetylfuranoside to β-Acetylfuranoside can be carried out according to the process of scheme 2 below:

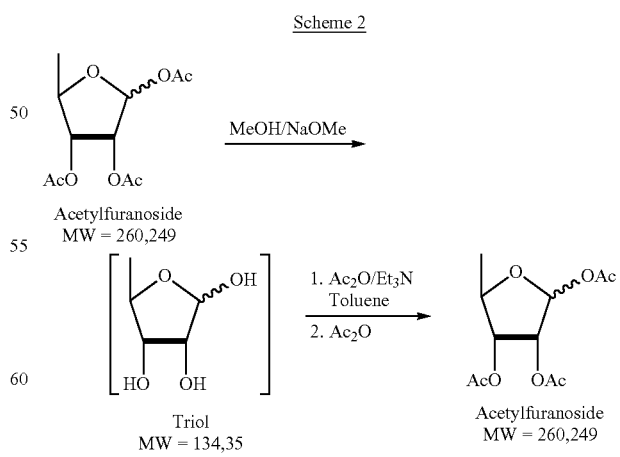

In a first step, solvent from the initial ACF synthesis (scheme 1) is distilled off. The following deacetylation is carried out with a suitable solvent such as aliphatic alcohols, preferably methanol and a suitable base such as alkali hydroxides or alkali alcoholates, preferably sodium methoxide, at reaction temperatures of 0° C. to −20° C., preferably at −5° C. to −10° C.

The reaction mixture is neutralized with an acid, preferably hydrochloric acid, up to pH 4-6, preferably 5. The alcohol is distilled off and the residue treated with a suitable solvent such as chlorinated hydrocarbons, preferably methylenchloride or aromatic hydrocarbons, preferably toluene.

After addition of an amine, preferably triethylamine, acetic anhydride is added slowly at batch temperatures of below 30° C., preferably 15° C. to 20° C. 4-dimethylaminopyridine and additionally acetic anhydride are added. The batch is quenched with water and a suitable solvent such as chlorinated hydrocarbons, preferably methylenchloride or aromatic hydrocarbons, preferably toluene is added.

The organic layer is separated and the aqueous layer several times extracted with the suitable solvent mentioned above. The combined organic layers are washed with an alkali solution, preferably sodium bicarbonate, leading to pH 8 after washing and further washed with water. The solvent is distilled off and β-ACF crystallized in suitable solvents such as aliphatic alcohols, preferably propan-2-ol. The crude product is recrystallized in a suitable solvent such as aliphatic alcohols, preferably propan-2-ol, resulting in white β-Acetylfuranoside crystals with a content of <2 weight-% of the α-anomer. The method described herein is also referred to as "Chemical Reprocessing" in FIG. 1 which further summarizes the present process.

BRIEF DESCRIPTION OF THE DRAWINGS

FIG. 1: Process flow chart summarizing the process according to the present invention

EXAMPLES

The invention is now further illustrated by the followings working examples, which are by no means intended to limit the scope of the present method.

Example 1

Distillative Recovery of β-Acetylfuranoside
Distillation 3000 kg Acetylfuranoside mother liquor (ratio α/β 35:65) was evaporated to an oil (residual solvent <1%) at 30 to 80° C. and 5 to 100 mbar (about 1000 kg residual oil). The residual oil was distilled under vacuum at 1 to 3 mbar and 200 to 210° C. steam heating temperature in a continuous thin-film evaporator resulting in 609 kg distillate (containing α/β-Acetylfuranoside) and about 400 kg residue.
Crystallization 1247 kg distillate (ratio α/β 35:65) was dissolved in 541 L propan-2-ol at 20 to 25° C. and cooled to −12 to −8° C. The resulting suspension was agitated for 6 hours to complete crystallization. The crystallizate was isolated and washed with cold propan-2-ol. 425 kg of white crude product was obtained (2-3% residual moisture).

755 kg of crude product was recrystallized from propan-2-ol (ratio 1:1) under the same conditions. Yield: 748 kg β-Acetylfuranoside.

Example 2

Chemical Conversion of α/β-Acetylfuranoside 811 kg Acetylfuranoside mother liquor (about 250 kg α/β-Acetylfuranoside) was concentrated by distillation to obtain an oily residue (ratio α/β 60:40). Then 1060 L of methanol was added and cooled to −8° C. 127 L of sodium methoxide was then added and stirred for 3 hours. The reaction mixture was neutralized with 126 L of semi concentrated hydrochloric acid to bring the pH to 5.1.

1235 L of solvents were distilled off 212 L of toluene; 322 L of triethylamine and 42 L of toluene were added. 265 L of acetic anhydride were added slowly, keeping the batch temperature between 15-17° C. The mixture was stirred at 16-17° C. for 1.5 hours. 6.06 kg of 4-dimethylaminopyridine and additionally 367 L of acetic anhydride were added. The batch was stirred for 1.5 hours. The reaction mixture was quenched with 212 L of water and 265 L of toluene were added. After the aqueous layer was separated, it was extracted 3 times with 265 L of toluene. The combined organic layers were washed twice with 550 L of saturated sodium bicarbonate solution, leading to pH 8 after washing, and 530 L of water. Toluene was then distilled off and 424 L of propan-2-ol were added and the residue dissolved. The solution was cooled to −9° C. for 6 hours. The crystallizate was isolated and washed with cold propan-2-ol. 205.2 kg of white product were obtained (2-3% residual moisture). Finally, the crude product was recrystallized with 205 L of propan-2-ol. Yield: 187.8 kg β-Acetylfuranoside.

What is claimed:

1. A method for recovery of initially not separated β-acetylfuranoside from mother liquor remaining from the synthesis of acetylfuranoside (ACF), comprising the following sequential steps:
    a) Evaporation to less than 1% residual solvent of the mother liquor remaining from an initial synthesis of ACF, to increase the content of residual α/β-ACF from about 8 to 15 weight-% to about 25 to 45 weight-%, followed by distillation to about 60 to 80 weight- and subsequent crystallization of β-ACF out of the distillate by adding a suitable solvent;
    b) Chemical conversion of α/β-ACF mixture remaining in the mother liquor of step a), to β-ACF by de-acetylation and subsequent re-acetylation, followed by crystallization of β-ACF by addition of a suitable solvent;
    c) Optional repetition of step a) and b) in a sequential (clockwise) cyclic process; wherein the distillation to about 60 to 80 weight-% of step a) is carried out at 1 to 3 mbar and 200 to 210° C. heating temperature in a continuous thin film evaporator.

2. The process according to claim 1, wherein step b) comprises the de-acetylation of α/β-ACF in the presence of a suitable base, followed by neutralization with a suitable acid and further followed by the re-acetylation reaction in the presence of suitable base, a suitable catalyst and a suitable acetylating agent.

* * * * *